United States Patent [19]

Mansson

[11] 3,972,228
[45] Aug. 3, 1976

[54] ULTRASONIC NON-DESTRUCTIVE PULSE TESTING APPARATUS

[75] Inventor: Sven E. Mansson, Hollviksnas, Sweden

[73] Assignee: Magnetic Analysis Corporation, Mount Vernon, N.Y.

[22] Filed: July 15, 1974

[21] Appl. No.: 488,473

[52] U.S. Cl. ................................ 73/67.7; 330/21; 330/32
[51] Int. Cl.² ......................................... G01N 29/04
[58] Field of Search ........... 73/67.7, 67.5 R, 67.8 R, 73/67.9, 71.5 US; 330/21, 32, 31; 315/392, 395; 178/7.5 SE

[56] References Cited
UNITED STATES PATENTS

| | | | |
|---|---|---|---|
| 2,555,163 | 5/1951 | Schneider | 315/392 |
| 2,695,381 | 11/1954 | Darling | 330/32 X |
| 2,811,590 | 10/1957 | Doremus et al. | 330/32 X |
| 2,871,404 | 1/1959 | Mugele | 73/67.7 X |
| 2,949,028 | 8/1960 | Joy | 73/67.9 |
| 3,287,963 | 11/1966 | Stanya et al. | 73/67.9 |
| 3,323,353 | 6/1967 | Munger | 73/67.8 R |
| 3,348,410 | 10/1967 | Henry | 73/67.8 |
| 3,350,942 | 11/1967 | Peltola | 73/67.8 R |
| 3,576,126 | 4/1971 | Weighart | 73/67.7 |
| 3,646,805 | 3/1972 | Walters | 733/67.9 |
| 3,667,287 | 6/1972 | Furon | 73/67.9 |
| 3,673,325 | 6/1972 | Uphoff | 73/67.7 X |
| 3,733,891 | 5/1973 | Weighart | 73/67.9 |

OTHER PUBLICATIONS
Crawford, Science and Electronics, June–July 1970, pp. 33–35.
Carlin, Ultrasonics, pp. 222–225, 234–235, 260, McGraw-Hill Book Co., 1960.

Primary Examiner—Richard C. Queisser
Assistant Examiner—Stephen A. Kreitman
Attorney, Agent, or Firm—Pennie & Edmonds

[57] ABSTRACT

Apparatus is described including means for generating short driving pulses for an ultrasonic transducer which are of selectable PRF and highly stable. A multi-stage amplifier for received signals comprises emitter-follower transistors of approximately unity gain coupled by step-up transformers. Expanded sweeps for a cathode-ray tube (CRT) display are produced from initial ramps synchronized with the driving pulses, and supplied through a variable attenuator to a limiter. Signal gates of adjustable position and width are produced from the sweeps and maintain their relative positions with respect to the sweeps during expansion. A threshold control circuit is gated to yield output signals for an alarm, etc. when received signals within the gate exceed an adjustable threshold level, and also produces a display signal gate for the CRT which accurately indicates the displayed echo amplitude required to actuate the threshold circuit. The received signals and display gate are supplied to the CRT on alternate sweeps and have coinciding baselines. Marker pulses are applied to both sets of sweeps on the same baseline.

17 Claims, 8 Drawing Figures

ULTRASONIC NON-DESTRUCTIVE PULSE TESTING APPARATUS

BACKGROUND OF THE INVENTION

Ultrasonic non-destructive pulse testing apparatus is known in which an ultrasonic transducer is pulse driven to apply ultrasonic pulses to an object to be tested, and received signals corresponding to variations or defects in the object are displayed on a cathode-ray tube (CRT) and used to actuate indicating apparatus such as an alarm, marker, recorder, etc. Commonly the received signals are echoes reflected back from the front and rear surfaces of the object, and from flaws, defects, discontinuities or other variations in the object between front and rear surfaces.

A single ultrasonic transducer is often used for transmission and reception, although separate transducers may be employed. Instead of receiving echoes, transmitter and receiving transducers may be placed on opposite sides of the object, and changes in the received signals used to detect variations or defects in the object. To facilitate applying the ultrasonic pulses to the object, and receiving signals therefrom, a couplant such as water, oil, etc. is usually introduced between the transducer(s) and the object under test. Relative movement between transducer(s) and object may be used to scan various portions of the object.

In such apparatus highly stable driving pulses are important. It is also desirable to provide a range of PRF's (pulse recurrence frequencies) in order to meet various requirements encountered in practice. Thus thicker objects may require lower PRF's than thinner objects since it will take longer for the ultrasonic waves to pass through the object. At each PRF, however, stability should be maintained.

Received signals may be very small, perhaps 1 or a few microvolts. Consequently high amplification is necessary, and high stability with low noise level is important, as well as adequate bandwidth to enable very short high frequency driving pulses to be employed.

Signals gates have been described which utilize a delayed transmitter pulse, or a front surface pulse, to start the gate. The gates may be used to select echoes in a region of interest within the object for actuating an alarm when the echoes exceed a threshold level. It has been suggested to display such gates on the same sweeps as the echoes, in which case the echoes ride on the top or bottom of the gate, depending on the gate polarity. Also, any noise present will also ride on the gate. This increases the difficulty in measuring the echo amplitude, since the gate amplitude must be taken into account. It has been suggested to display the received echoes and gate on alternate sweeps, particularly with the gate baseline offset from the sweep baseline and echoes within the gate displayed on the gate.

Expanded sweeps have been suggested for displaying an expanded portion of the complete echo signal on the face of the CRT. Such expansion may cause the desired portion to move off the screen, thus requiring further adjustment.

Time markers impressed on the sweeps have also been suggested, either on the same sweeps as the echoes or on alternate sweeps.

The present invention is directed to the provision of ultrasonic pulse testing apparatus having improved means for generating driving pulses, amplifying received signals, displaying the received signals and signal gate with marker pulses, and producing expanded sweeps.

SUMMARY OF THE INVENTION

In accordance with a presently preferred embodiment of the invention, pulses of selectable PRF are produced by a tunable sine wave oscillator feeding a square wave generator, and a pulse divider circuit which periodically supplies an excursion of one polarity of the square wave to an output circuit to produce a pulse train having a PRF which is a sub-multiple of the square wave frequency. An adjustable time constant circuit selects the desired sub-multiple. A second pulse divider supplied from the first may be used to obtain still lower PRF's. The pulse train is then supplied to differentiating and amplifier circuits to produce short driving pulses for the ultrasonic transducer.

Received signals are supplied to a clipper and amplifier, and advantageously a multi-stage transistor amplifier is employed in which each stage is an emitter-follower having approximately unity gain with a step-up transformer connecting the output of one emitter-follower to the input of the next. In this way high gain and wide bandwidth can be obtained with high stability and low noise level.

The amplified signals are supplied to cathode-ray tube means for display. Horizontal sweeps are developed, with provision for expansion of selected regions of interest in the complete received video signal. Advantageously, initial ramps are generated which are of predetermined amplitude and synchronized with the transducer driving pulses. The ramps are applied through variable attenuator means to limiter means having a limit level less than the ramp amplitude. By adjusting the attenuator means, sweeps of different time duration but of the same peak amplitude can be developed. These are amplified and supplied to the CRT.

The sweeps are also used to develop a signal gate of adjustable position and width, and which will maintain its position on the CRT display as the sweeps are expanded. To this end, the peaks of the sweeps are clamped at an adjustable first level which is less than the sweep amplitude with respect to a reference level (usually ground). A second adjustable level is established intermediate the reference and first levels. Switch circuit means produces a signal gate during the portion of a sweep lying between the reference and second levels.

In the specific embodiment, the first (clamping) level determines the position of the trailing edge of the gate with respect to the beginning of the sweep, and the second level determines the gate width. As explained hereinafter, if the sweep is expanded to spread out the echoes in a given region of interest, without changing the gate levels, the gate position and width as displayed on the CRT will be substantially unchanged. This greatly facilitates selection and expansion of the region of interest, without requiring readjustment to maintain the gated region on the screen. After expansion, the gate position and width can be readjusted, if desired, to encompass the desired signal range.

The received signals and the signal gate are also supplied to a threshold control circuit to yield output indicator signals for actuating an alarm, marker, recorder, etc. whenever received signals within the gate exceed an adjustable threshold level. It is considered highly desirable to display the signal gate on the CRT in such a manner that its amplitude indicates the level of received signals which will actuate the threshold circuit. Accordingly, the threshold control circuit is designed to develop a display signal gate for the CRT which varies with the threshold level and takes into account differences in the amplitudes of displayed signals and the effective amplitudes of the corresponding signals in the threshold control circuit.

Advantageously the display signal gate and the received signals are displayed on alternate sweeps of the CRT and have coinciding baselines. Thus the operator can readily observe which signals will actuate the threshold circuit, and adjust the threshold level accordingly.

Marker pulses may also be displayed. These are advantageously developed from predetermined edges of the square wave from which the transducer driving pulses are developed, and displayed on the baselines of both received signal and signal gate sweeps to yield bright markers which are readily observable against the received signal pattern.

Further features of the invention will in part be described in, and in part be understood from, the following detailed description of a specific embodiment. It will be understood that certain features of the invention may be employed and others omitted, if desired, as meets the requirements of a particular application or the judgment of the designer.

DETAILED DESCRIPTION OF THE SPECIFIC EMBODIMENTS

Figure 1:
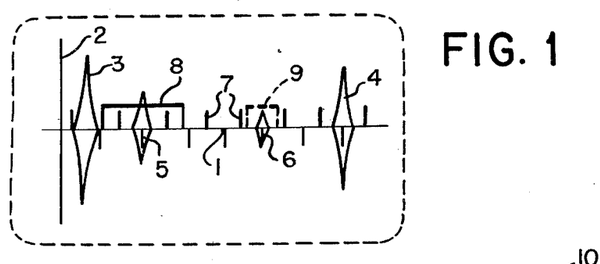
FIG. 1 illustrates an example of a display on the face of the cathode-ray tube in accordance with the invention.

Referring to FIG. 1, an illustrative cathode-ray tube display in accordance with the invention is shown. The baseline for vertical deflection is shown at 1. A-C transmitted and echo signals are here displayed, and extend above and below the baseline, although detected signals extending in only one direction could be displayed. The driving pulse is shown at 2, and front and rear surface echoes at 3 and 4. Echoes due to flaws or other variations in the object under test are shown at 5 and 6. Calibration markers are shown at 7, evenly spaced along the baseline.

A signal gate of adjustable position, width and amplitude is displayed in full lines at 8 and in dotted lines at 9, corresponding to the regions of interest to the operator. The signal gate and echoes are displayed on alternate horizontal sweeps so that the echoes and noise (not shown) remain centered on the baseline and do not ride on top of the signal gate. The top of the signal gate corresponds to the threshold level of echoes which will actuate an alarm or otherwise be indicated. Thus with echo 5 extending above the top of signal gate 8, it will be indicated. However, echo 6 is below the top of signal gate 9, and will not be indicated. If the operator considers that echo 6 should be indicated, he can lower the level of the gate until the echo reaches or extends above the gate top.

As will be explained hereinafter, once the signal gate has been positioned at a region of interest, the display can be expanded to display that region on a larger horizontal scale while assuring that the gate does not move off the screen.

Figures 2, 3, 5:
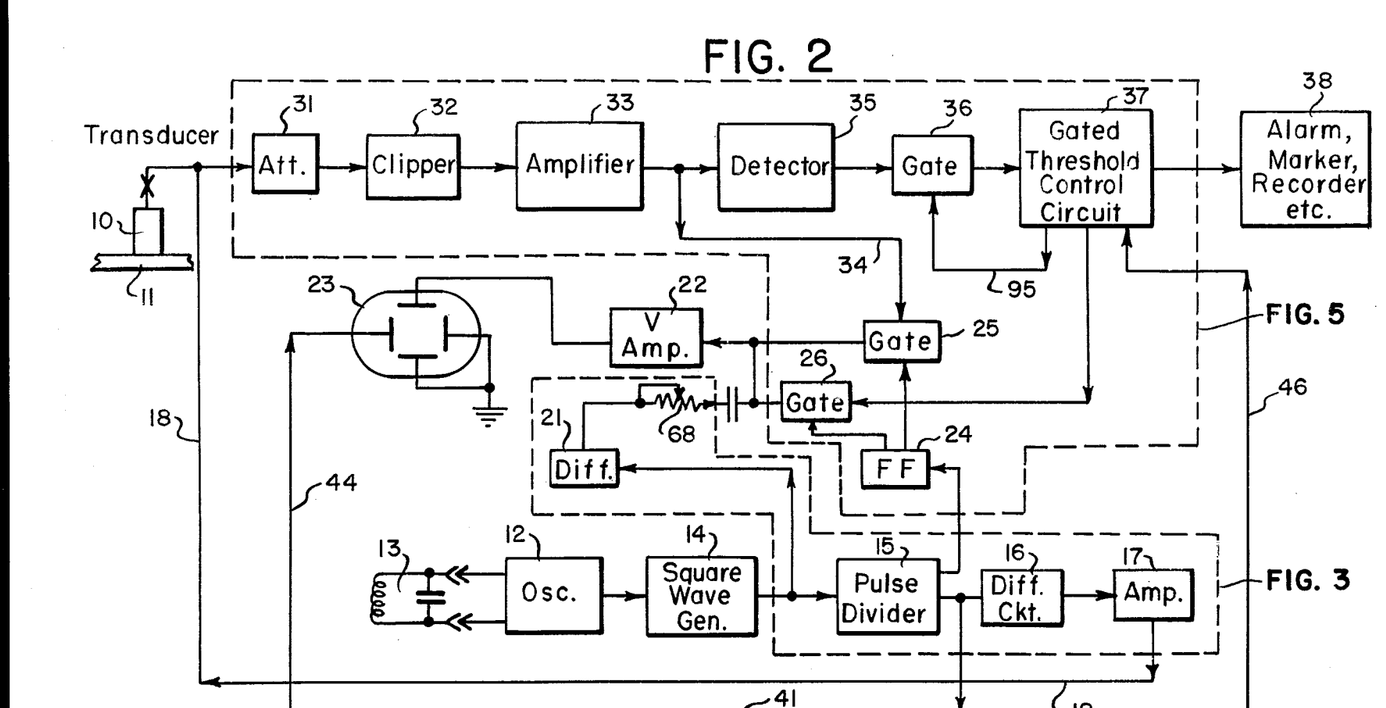
FIG. 2 is a block diagram of apparatus in accordance with the invention.
FIG. 3 is a schematic circuit diagram of a portion of the transmitter pulse generator.
FIG. 5 is a schematic circuit diagram of the receiver and threshold control circuits.
Figure 3:
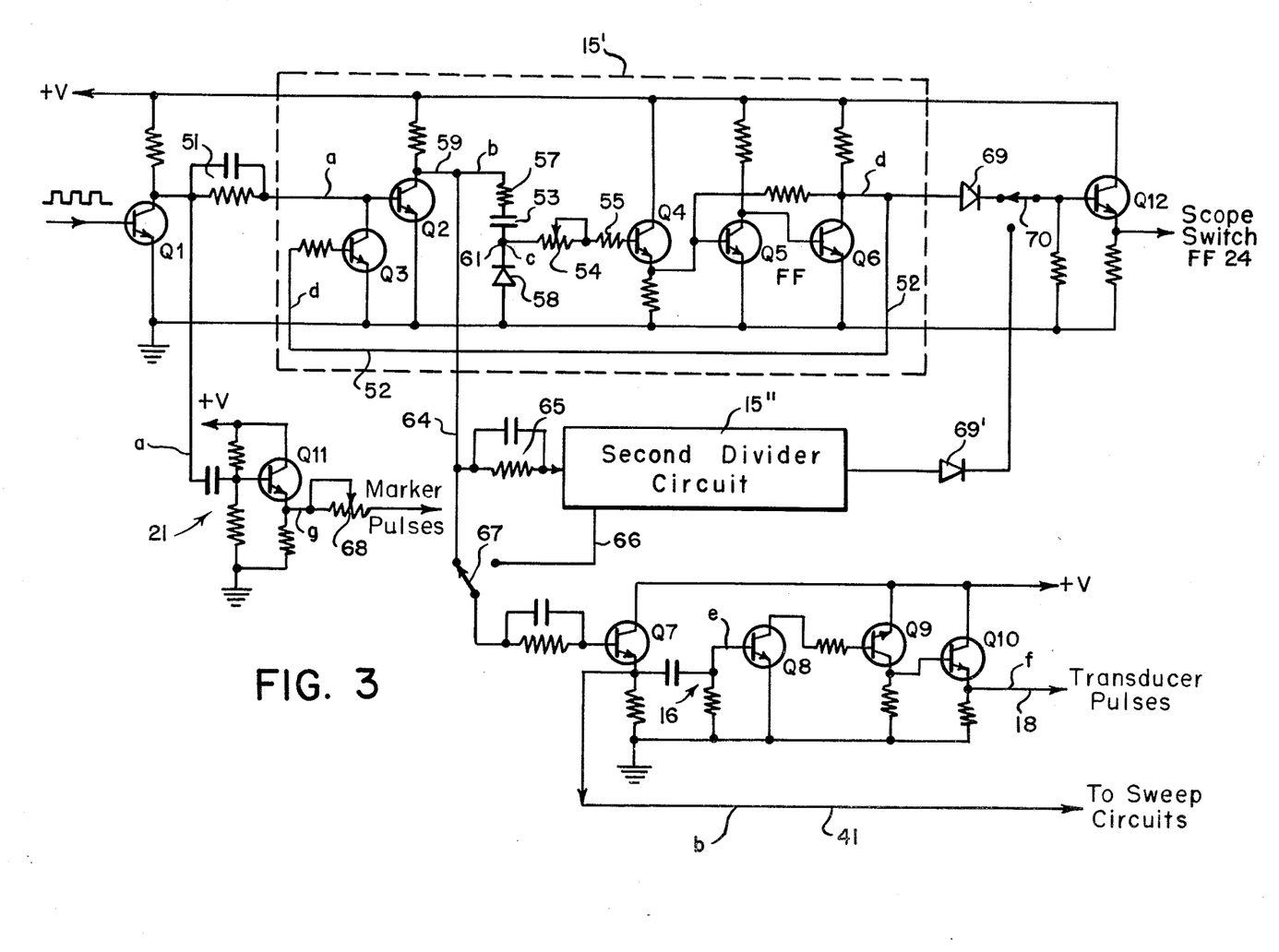

Referring to FIG. 2, an ultrasonic transducer 10 is shown in position to test an object 11. The transducer may be selected from various types known in the art and a suitable acoustic couplant such as water, oil, etc. may be employed between the transducer and the object. For some applications the transducer may be considerably spaced from the object.

Driving pulses for the transducer are generated by circuits including a sine wave oscillator 12 tuned by a switchable tank circuit 13. The sine wave output is converted to a square wave in 14, and the square wave is supplied to a pulse divider 15 to yield a train of spaced pulses at the desired PRF. The output of 15 is applied to a differentiating circuit 16 which yields very short pulses which are amplifier in 17 and supplied through line 18 to drive transducer 10.

The square wave output of 14 is differentiated in 21 to form short marker pulses which are supplied to vertical amplifier 22 for display on the face of cathode-ray tube 23. Pulses from divider 15 are supplied to flip-flop 24 which alternately opens and closes gates 25 and 26 to supply received echoes and a display signal gate to amplifier 22 for display on alternate sweeps of CRT 23. These circuits will be described more fully hereinafter.

Received echoes from transducer 10, as well as the drive pulses in line 18, are supplied through an attenuator 31 to a clipper 32 which limits the peak excursions to a desired small value. The signals are amplified in 33 and supplied through line 34 to gate 25 for display on alternate sweeps of CRT 23. The output of amplifier 33 is also supplied to a detector 35.

Detected echoes in a selectable region of interest are supplied by gate 36 to a gated threshold control circuit 37 which produces indicating outputs whenever the echoes exceed a selectable threshold amplitude. The outputs of 37 may be used to actuate an alarm, marker, recorder, etc., as desired, as indicated at 38.

Horizontal sweeps for CRT 23 are developed by supplying the output of pulse divider 15 through line 41 to a ramp generator 42 which produces initial ramps synchronized with the drive pulses. The output of 42 is fed to a sweep expansion circuit 43 which supplies sweeps through line 44 to CRT 23. The sweeps from 43 are also supplied to a gate generator 45 to develop a signal gate which is manually adjustable in position and width for selecting the region of interest in the complete echo signal. The signal gate from 45 is supplied through line 46 to the threshold control circuit 37 which controls gate 36 and also produces a display signal gate for CRT 23.

Figure 4:
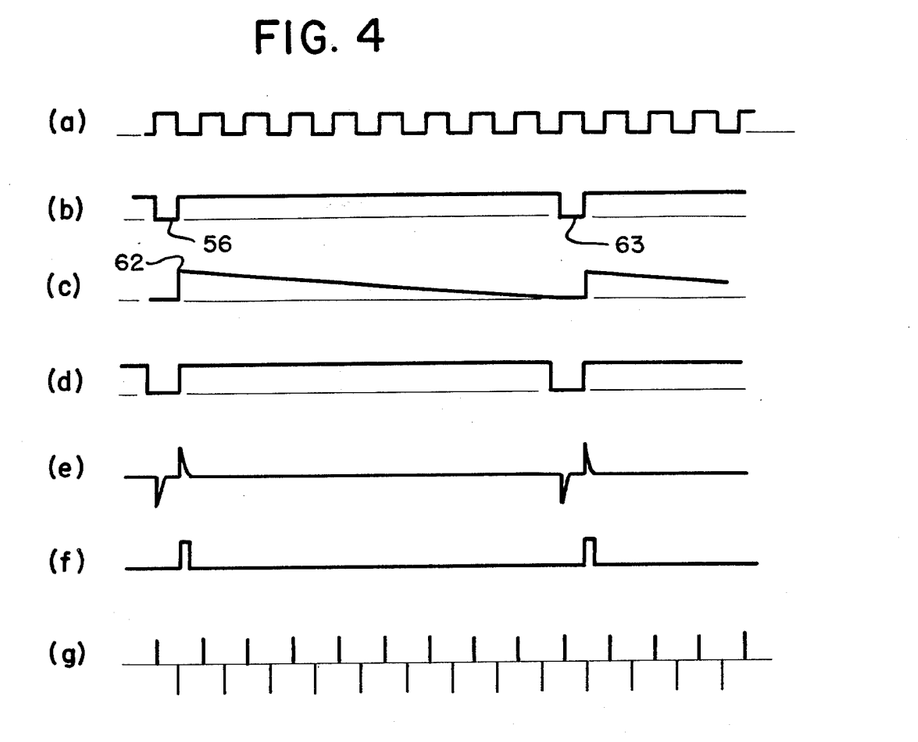
FIG. 4 shows waveforms applicable to FIG. 3.
Figure 5:
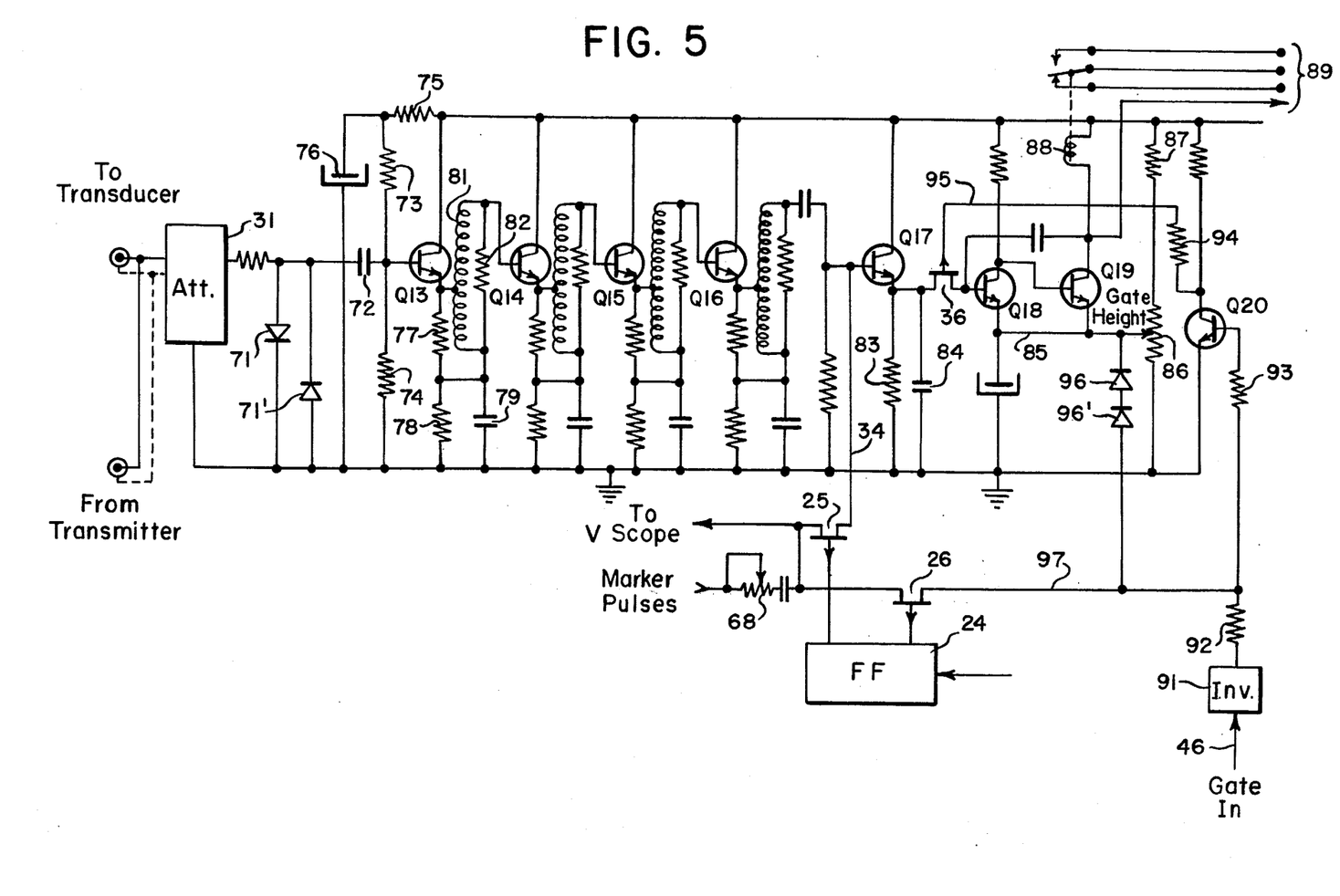

Referring to FIG. 3, letters *a – g* refer to corresponding waveforms of FIG. 4. FIG. 4 is primarily a timing diagram and relative amplitudes may differ from those shown. In FIG. 3, as well as in subsequent figures, transistors of the NPN type are shown with the emitter arrow pointing away from the base, and vice versa for those of the PNP type. The types may be selected as desired, with appropriate change in voltage polarity, as is well known in the art.

Q1 is the output transistor of the square wave generator 14 of FIG. 2, and supplies a square wave through a coupling circuit 51 to a first pulse divider circuit shown in block 15'. The square wave $a$ is applied to the base input of Q2. Q3 is normally on (conducting) by a positive voltage in line 52 and short-circuits the input of Q2, thereby preventing the production of output pulses by Q2. The short-circuit is periodically removed by substantially grounding line 52 to turn Q3 off (nonconducting), thereby allowing one positive excursion of the square wave to pass to the collector output of C2, with inversion, as shown at $b$.

The control of Q3 includes an adjustable time constant circuit including primarily capacitor 53, variable resistor 54 and resistor 55. When Q2 conducts to yield output pulse 56 (FIG. 4$b$), capacitor 53 is substantially completely discharged through the collector-emitter path of Q2, small resistor 57 and diode 58. At the end of pulse 56, line 59 goes high and supplies a charging voltage to the time-constant circuit. Accordingly the voltage at point 61 goes high as shown at 62 in FIG. 4$c$. This forward biases Q4 and turns Q5 on. Q5 and Q6 are connected as flip-flop (FF) and consequently Q6 is off. The collector Q6 will therefore be high and the positive voltage in line 52 will turn on Q3 to short-circuit the input of Q2. Capacitor 53 will start to charge through resistors 54, 55 and the base-emitter circuit of Q4, the rate of charging being adjustable by resistor 54. Accordingly the voltage at point 61 will gradually decrease as shown in $c$. As the capacitor approaches full charge, the voltage at 61 becomes too low to maintain base-emitter current in Q4. Q4 then turns off, thereby turning Q5 off and Q6 on. The resultant low voltage in line 52 turns Q3 off to remove the short circuit at the input of Q2, thereby allowing Q2 to conduct on the next positive excursion of square wave $a$ to yield output pulse 63 in $b$ and discharging capacitor 53. The operation then repeats.

The charging time constant may be adjusted to cause Q4 to turn off between predetermined positive excursions of square wave $a$ so that precise division is obtained. Division ratios of 10:1 or 12:1 have been employed in practice. For a higher division ratio the slope of wave $c$ may become too gradual to assure precise division. If higher division is desired, a second divider circuit 15'' may be fed with the output train of pulses $b$ in line 64 through a coupling circuit 65 and a further division performed. Divider 15'' may be like divider 15', with a larger capacitor 53 to produce a longer time constant. The output is supplied through line 66 to switch 67 so that either output can be selected.

The selected pulse output is supplied through a coupling circuit to Q7 functioning as an emitter-follower, and then to a C-R differentiating circuit 16. For convenience of explanation it will be assumed that pulse output $b$ in line 64 is selected. The differentiation produces short spikes $e$ at the leading and trailing edges of $b$. The negative spikes are ineffective at the input of Q8, but the positive spikes are amplified and clipped in Q8 and Q9, the latter being of the PNP type. The output of Q9 is supplied to emitter-follower Q10 to produce driving pulses in line 18 as shown at $f$. These are supplied to transducer 10 (FIG. 2).

The length of the driving pulses may be selected as desired. Pulses of the order of 40 nanoseconds have been employed, and serve to drive transducers having frequencies in the megacycle region. The frequency of oscillator 12 (FIG. 2) may be selected as desired, for example in several steps up to, say, 50 KHz.

The square wave $a$ from Q1 is also supplied to a C-R differentiating circuit 21 at the input emitterfollower Q11, and the positive and negative spikes produce marker pulses $g$ at the emitter output. These are fed through a variable resistor 68 to the vertical amplifier 22 (FIG. 2) for display on the CRT sweeps.

The wave $d$ from Q6 is divider 15', and a similar wave from divider 15'', are fed through respective diodes 69, 69' to emitter-follower Q12 whose output switches FF24 (FIG. 2) at each pulse occurrence. Switch 70 may be actuated with switch 67 to connect either divider to Q12.

Referring to FIG. 5, drive pulses and echo signals from the transducer are fed through an attenuator 31 to a clipper circuit comprising oppositely poled diodes 71, 71'. This clips the large amplitude drive pulses to, say, 0.1 volt, while passing small echoes. The resultant signals are A-C coupled through capacitor 72 to a multistage amplifier including transistors Q13–Q16. Each stage operates as an emitter-follower having approximately unity voltage gain, and is coupled to the next stage by a step-up transformer which yields the desired gain per stage. The stages are similar so that only the first need be described in detail.

The base of Q13 is biased by voltage-divider resistors 73, 74 from a decoupling circuit 75, 76 in the power supply. The emitter circuit includes a load resistor 77 and a bias resistor 78 shunted by capacitor 79. A step-up autotransformer 81 is connected across load resistor 77 and is shunted by a resistor 82 to yield the desired bandwidth. The stepped-up voltage is supplied to the base of Q14 for further amplification in the next stage. The base of Q14 is biased from the emitter of Q13 by the D-C connection provided by the autotransformer. The bases of the transistors in subsequent stages are likewise biased through the base-emitter paths of the preceding stages, respectively, so that only one initial biasing circuit suffices to bias the bases of all the amplifier stages.

With unity gain in the emitter-followers and a gain of 10 in the step-up transformers, for example, the four stages shown will yield a gain of about 10,000. More stages are likely to be employed in practice, say six stages yielding a gain of about 1 million. Very stable operation is possible with low noise level, which is particularly desirable in amplifying small echoes. The outputs of all stages are substantially in phase so that adverse feedback problems are reduced. Although the stages are D-C coupled, drift problems are largely avoided and relatively few components are required to produce high-gain linear amplification.

If desired, and depending on the frequency and bandwidth requirements of a particular application, theh transformers may be tuned by shunt capacitors.

The output of the amplifier is supplied to Q17 connected as a so-called "infinite impedance" detector with an emitter resistor 83 shunted by capacitor 84 selected to yield a high input impedance to the detector. As here shown, positive detected excursions of the A-C echoes are supplied through an FET gate 36 to a threshold trigger circuit comprising Q18 and Q19 connected as a one-shot multivibrator.

The threshold level is established by the voltage in line 85 which is adjustable by potentiometer 86 connected to the power supply through resistor 87. Normally Q18 is off and Q19 on. When a signal through gate 36 exceeds the threshold level, Q18 is turned on and Q19 off. The change in current through Q19 is sensed by relay 88 and lines generally designated as 89 may be connected to suitable alarm, marker, recorder or other indicating apparatus, as shown in FIG. 2. If desired, relay 88 may be replaced by a resistor and only the collector output of Q19 used for indication. At the end of the echo, Q18 is turned off and Q19 on, ready for another echo exceeding the threshold level.

In order to record only echoes within the region of interest, the signal gate from gate generator 45 is supplied through line 46 to the threshold control portion of FIG. 5. As will be described in connection with FIGS. 7 and 8, this is a negative-going gate. It is inverted in 91 to produce a positive-going gate, and through resistors 92, 93 to the base of Q20. Q20 is turned on during the gate interval, and the low collector voltage applied through resistor 94 and line 95 to the gate 36 turns the FET on. Therefore echoes are supplied to the trigger circuit Q18, Q19 only during the signal gate interval.

As before stated, it is desired to display on the CRT the signal gate with the top of the gate indicating the level of the echoes which will actuate the trigger circuit. Although the voltage in line 85 establishes the threshold level, it does not accurately correspond to the amplitude of the displayed echoes which will actuate the trigger circuit. The displayed echoes are taken from the base of Q17, and supplied through line 34 and FET gate 25 to the CRT. To actuate the trigger circuit the echo amplitude at the base of Q17 must exceed the voltage of line 85 by the base-emitter threshold voltages of Q17 and Q18. For silicon transistors the threshold voltage is about 0.6 volt, so that the amplitude difference is about 1.2 volts. Assuming a threshold of a few volts in line 85, the difference may be significant. Accordingly a pair of diodes 96, 96′ are connected between lines 85 and line 97. The diodes are chosen to have threshold voltage substantially equal to those of the transistors, i.e. 0.6 volt in this example, provided by silicon diodes. Therefore the voltage level of the top of the gate in line 97 exceeds that in line 85 by 1.2 volts.

Figure 6:
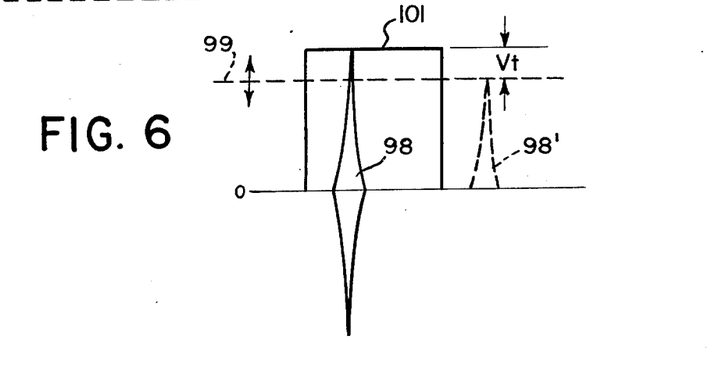
FIG. 6 shows waveforms applicable to FIG. 5.

The operation is further expained in FIG. 6. Here echo 98 is assumed to be supplied through line 34 to the CRT. The corresponding dotted detected echo 98′ represents the effective amplitude of the echo to actuate the trigger circuit when the threshold level in line 85 is that shown by dotted line 99. Voltage $V_t$ represents the difference in amplitude of echoes 98 and 98′. With the sum of the threshold voltages of diodes 96, 96′ equal to $V_t$, the top of signal gate 101 as supplied to the CRT through line 98 will correspond to the amplitude of echo 98. Thus the display signal gate 101 has an amplitude substantially equal to the minimum amplitude of received signals as displayed on the CRT which will actuate the threshold circuit, and, the operator can use the top of the displayed signal gate to indicate the echo amplitude required to actuate the alarm, etc.

Figure 7:
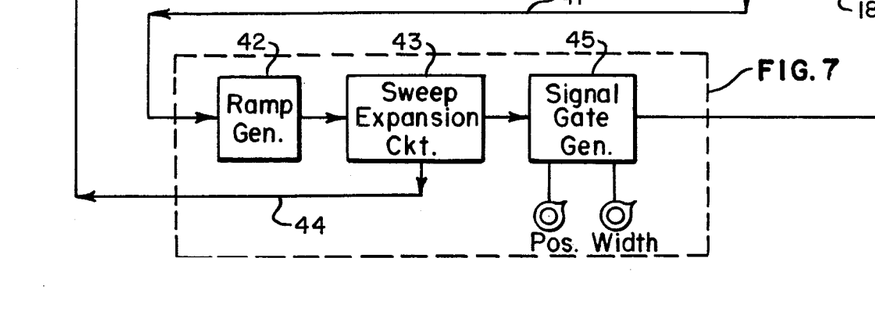
FIG. 7 is a schematic circuit diagram of the sweep and gate generating circuits.
Figure 8:
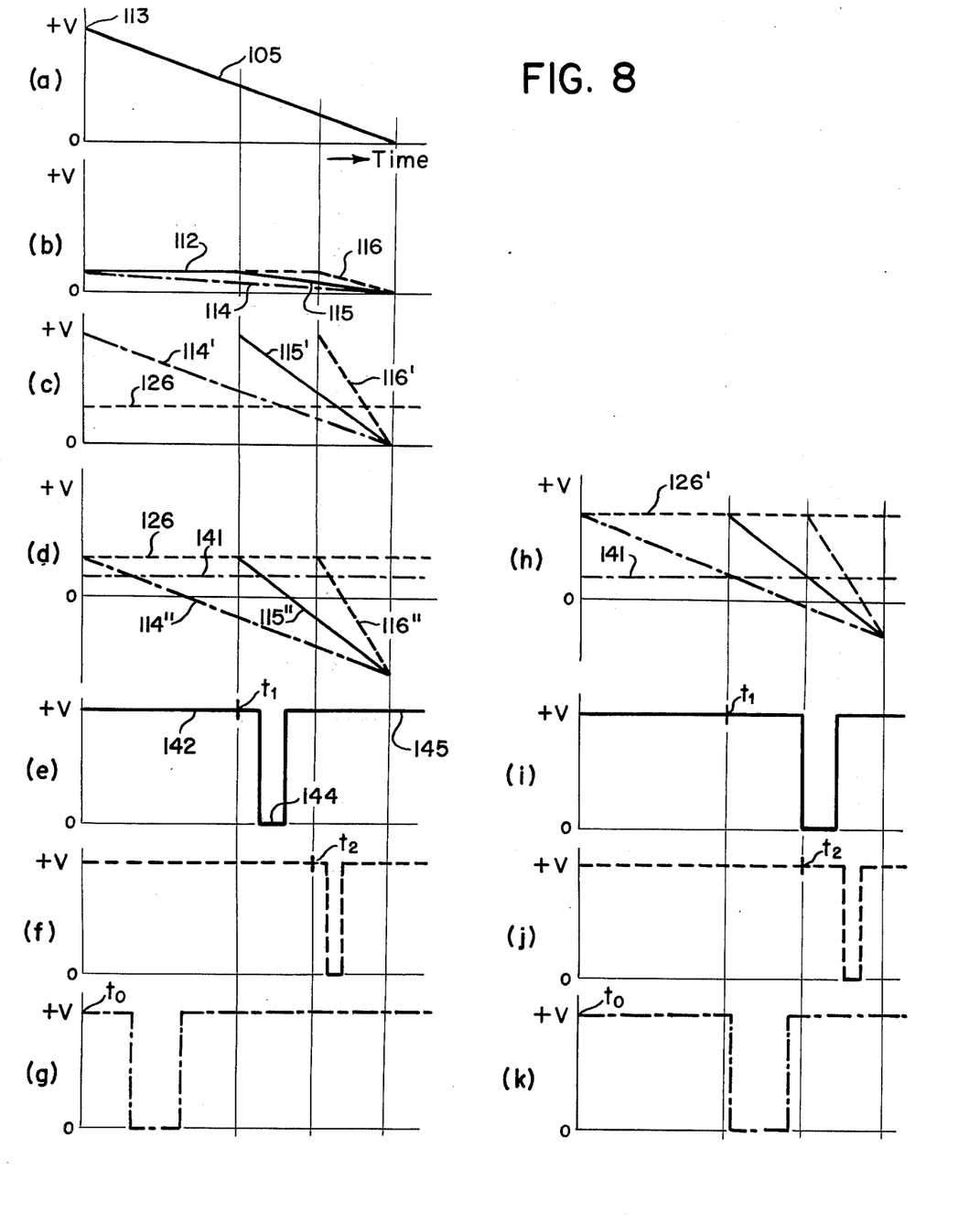
FIG. 8 shows waveforms explanatory of the operation of FIG. 7.

Referring to FIG. 7, wave b of FIG. 4 is supplied through capacitor 102 and coupling circuit 103 to the base of Q21 (PNP). Accordingly, sweep capacitor 104 is charged to substantially +V during the pulse interval, e.g. 56. At the end of the pulse, Q21 is turned off, and capacitor 104 discharges through Q22. Q22 is an FET connected to pass a constant current during the discharge. This yields an initial linear ramp voltage 105 as shown in FIG. 8a. The duration of ramp 105 may be selected to correspond to the maximum sweep time desired for the CRT.

The ramp is supplied to Q23 and Q24 connected as a cascaded emitter follower to provide a high input impedance. The emitter circuit of Q24 includes variable attenuator means, here shown as a delay potentiometer 106 in series with resistor 107 which limits the range of adjustment. The slider of the potentiometer is connected through diode 108 to the base of Q25. Limiter means, here shown as a Zener diode 109, establishes an upper limit of the voltage in line 111. By adjusting 106, any desired latter portion of ramp 105 can be selected for developing an expanded CRT sweep.

This is illustrated in FIG. 8b. Horizontal line 112 indicates the Zener limited voltage level which is considerably lower than the initial voltage 113 of ramp 105. By turning potentiometer 106 down, the initial ramp voltage can be brought down to the limit level, yielding a full length sweep as shown at 114 in dot-dash lines. At a mid-position the first half of ramp 105 is limited, and only the latter half produces a sweep 115 shown in full lines. At a higher adjustment, only the latter quarter of ramp 105 produces dashed sweep 116. Thus delayed sweeps of adjustable time duration and slope are produced.

Q25, Q26 and Q27 amplify the selected portion (or all) of the initial ramp. Accordingly, at point 117 sweeps will be produced of full amplitude but of shorter time duration than the initial ramp 105, the delay in initiation being controlled by potentiometer 106. These are shown in FIG. 8c in corresponding types of lines at 114′–116′. The expanded (or non-expanded) sweeps are supplied through line 44 to the horizontal deflection plates of CRT 23 (FIG. 2).

To develop the signal gate, the sweeps at point 117 are supplied through capacitor 118 to a clamping circuit which clamps the maximum positive excursions to an adjustable level. Thus the sweeps are supplied through diode 119 to the slider of potentiometer 121 connected across the power supply through resistors 122, 123 which limit the range of adjustment between desired levels. Capacitor 124 prevents variations in the adjusted level. Potentiometer 121 controls the position of the signal gate with respect to the sweep and is denoted "Gate Pos."

FIG. 8c shows a clamping level 126 and the respective sweeps at point 117. Capacitor 118 will charge to the difference between peak and clamping levels, thereby displacing the sweeps negatively as shown at 114″–116″ in FIG. 8d, for respective sweeps. For example, if the sweep amplitude at point 117 is 30 volts and the clamping level is 10 volts, the sweeps in line 125 will start at +10 volts and end at −20 volts.

Line 125 is connected through opposite-poled diodes 127, 128 to the base of Q28, with the point 129 connected to +V through resistor 131. The collector of Q28 is connected through diode 132 to the base of Q29. Line 125 is also connected through diode 133 and resistor 134 to +V, with the intermediate point connected through diode 135 to the base of Q29. The emitter of Q29 is connected to "GATE WIDTH" potentiometer 136, and the range of control of the latter is limited by resistors 137, 138 connected in series across the power supply. The collector of Q29 is connected through a constant current FET Q30 to the base of Q31 (PNP). The output gate signal in line 46 is developed across resistor 139 in the collector circuit of Q31.

To explain the operation, assume that the gate width potentiometer is set at a voltage 141 in FIG. 8d which is lower than 126. Considering sweep 115", initially the voltage in line 125 will be above the level 141. Line 143 will be nearly at level 141, since diode 135 and the base-emitter path of Q29 are forward-biased from +V through resistor 134. Consequently diode 133 will be back-biased and will not conduct. The forward bias to Q29 will turn it on. This will turn Q31 on through FET Q30 and the output in line 46 will be high, as shown at 142 in FIG. 8e. During this initial portion of the sweep, Q28 will be on due to current flow through resistor 131 and diode 128 to its base. Consequently diode 132 will be back-biased. The voltage at point 129 will be near ground, and diode 127 will be back-biased.

As the sweep voltage in line 125 goes below level 141, diode 133 will become forward-biased and cause line 143 to go below level 141. This will back-bias diode 135. Diode 128 and Q28 will remain forward-biased, and diode 127 will remain back-biased. With Q28 on, diode 132 will remain back-biased. Current to the base of Q29 will be reduced sufficiently to turn off Q29. The resultant high resistance of Q29 and the effective resistance of FET Q30 reduce the base-emitter current in Q31 sufficiently to turn off Q31. Thus the output will go low in line 46, as shown at 144 in FIG. 8e, thereby initiating the gate.

When the sweep in line 125 goes below ground, diode 127 will be forward-biased and point 129 will go below ground. Consequently, diode 128 will be back-biased and Q28 will be turned off. Current from +V through diode 132 will be supplied to Q29 and turn it on. This will turn on Q31 and the output in line 46 returns to its high level, as shown in 145 in FIG. 8e, thereby terminating the gate. With line 125 below ground, diode 133 will be forward-biased to take line 143 below ground, thus maintaining diode 135 back-biased.

At the end of the sweep, the negative charge on capacitor 118 will keep Q28 off, and line 143 negative, ready for the next sweep.

The foregoing explanation disregards threshold voltages of the diodes and transistors, to avoid undue complexity. These may be taken into account, as will be understood by those skilled in the art.

Overall, in the signal gate generator the peaks of the sweeps at point 117 are clamped to an adjustable first level 126 set by potentiometer 121 which is less than the sweep amplitude with respect to a reference level, here ground level. An adjustable second level 141 set by potentiometer 136 is intermediate the reference and first levels. The circuits function as switch circuit means responsive to sweeps from the clamping means and the second level to produce one output level 144 during a sweep portion lying in the zone between substantially the reference and second levels, and a different output level 142, 145 during sweep portions lying outside this zone to thereby produce a signal gate.

The switch circuit means may be considered as comprising an output circuit means including Q29, Q30 and Q31 biased at the second level by potentiometer 136, and first and second control circuit means including 133, 135 and 127, 128, Q28, 132, respectively. With falling sweeps as specifically shown, the first control circuit actuates the output circuit to level 142 during sweep portions prior to reaching level 141 and the second control circuit actuates the output circuit to level 145 during sweep portions after reaching the reference level 0 (ground). During sweep portions within the zone between levels 141 and 0 (ground), the output circuit is actuated to level 144.

Several advantages are present in the expansion and signal gate generation circuits. One advantage is that the position and width of the signal gate, as observed on the CRT, remains substantially unchanged as the sweep is expanded, without requiring additional adjustments. This is illustrated in FIGS. 8a – 8g. Assuming the position and width levels are those shown at 126 and 141, the signal gate of 8e corresponds to expanded sweep 115". If the expansion is increased to 116", the signal gate is as shown in 8f. With the full sweep 114', the signal gate is as shown in 8g. Sweep 115" begins at time $t_1$, sweep 116" at $t_2$; and sweep 114" at $t_0$.

By similar triangles in FIGS. 8d, it can be shown that the ratio of time occurrences of the leading edges of the gates to the respective sweeptime durations is the same in FIGS. 8e, f and g, and similarly for the trailing edges. On the CRT display, all three sweeps will have the same length since the horizontal deflection voltages are the same, as shown in FIG. 8c. Consequently the observed positions and width of the gates on the CRT will be the same.

Another advantage is that either the position or the width of the signal gate can be changed substantially independently of the other. FIG. 8h is similar to 8d except that the position level has been raised to 126'. Accordingly, the sweeps fall below the width level 141 later, and the gates in 8i – 8k occurs later than in 8e – 8g, respectively. However, since the width level 141 has not been changed, the respective travel times from width level to ground level is unchanged. Therefore the width will be the same, but the position will be shifted to the right as observed on the CRT.

If the position level 126 in FIG. 8d is left unchanged, and the width level 141 raised (or lowered), the sweeps will go below ground level at the same time as before, so that the trailing edges of the gates will remain unchanged. However, the sweeps will go below the width level 141 earlier (or later), thus producing wider (or narrower) gates.

The invention has been described in connection with a specific embodiment containing several features which together provide an instrument of high stability and versatility. Detailed circuits have been described. It will be understood that certain features may be employed and others omitted, and the detailed circuitry changed, if desired.

I claim:

1. Ultrasonic non-destructive pulse testing apparatus which comprises
    a. pulse generator and transducer means for applying ultrasonic pulses to an object to be tested,
    b. said pulse generator means including a square wave generator and a pulse divider for producing driving pulses for said transducer means,
    c. means for receiving signals corresponding to variations or defects in an object under test,
    d. cathode-ray tube means supplied from the receiving means for displaying received signals,
    e. sweep generator means for producing sweeps of adjustable expansion for said cathode-ray tube means,
    f. said sweep generator means including means for generating initial ramps of predetermined amplitude and limiter means having a limit level less than said predetermined amplitude, g. variable attenuator means supplied with said initial ramps and having an output connected to said limiter means for producing sweeps of adjustable time duration, h. means for amplifying and supplying the sweeps to said cathode-ray tube means, i. signal gate generatoing means supplied with said sweeps and including clamping means for clamping the peaks of the sweeps at an adjustable first level with respect to a reference level which is less than the sweep amplitude, j. means for establishing an adjustable second level intermediate said reference and first levels, k. switch circuit means responsive to sweeps from said clamping means and said second level for producing one output level during a sweep portion in the zone between substantially said reference and second levels and a different output level during sweep portions lying outside said zone, to thereby produce a signal gate, l. an adjustable threshold control circuit supplied with received signals and with the signal gate from said signal gate generating means for producing output signals when received signals within the gate exceed the threshold of the control circuit, m. said threshold control circuit including means for producing from said signal gate a display signal gate having an amplitude substantially equal to the minimum amplitude of received signals supplied to said cathode-ray tube means which will actuate the threshold circuit to produce output signals therefrom, n. means for displaying said display signal gate on sweeps alternating with the sweeps displaying said received signals and having coinciding baselines, o. a marker generator supplied from said square wave generator for producing marker pulses at predetermined edges of the square wave, p. and means for displaying said marker pulses on both sets of alternating sweeps.

2. Ultrasonic non-destructive pulse testing apparatus which comprises a. pulse generator and transducer means for applying ultrasonic pulses to an object to be tested, b. means for receiving signals corresponding to variations or defects in an object under test, c. cathode-ray tube means supplied from the receiving means for displaying received signals, d. sweep generator means for producing sweeps of adjustable expansion of said cathode-ray tube means, e. said sweep generator means including means for generating initial ramps of predetermined amplitude and limiter means having a limit level less than said predetermined amplitude, f. variable attenuator means supplied with said initial ramps and having an output connected to said limiter means for producing sweeps of adjustable time duration, g. means for amplifying and supplying the sweeps to said cathode-ray tube means, h. signal gate generating means including clamping means for clamping the peaks of said sweeps at an adjustable first level with respect to a reference level which is less than the sweep amplitude, i. means for establishing an adjustable second level intermediate said reference and first levels, j. switch circuit means responsive to sweeps from said clamping means and said second level for producing one output level during a sweep portion lying in the zone between substantially said reference and second levels and a different output level during sweep portions lying outside said zone to thereby produce a signal gate, k. an adjustable threshold control circuit supplied with received signals and with the signal gate from said signal gate generating means for producing output signals when received signals within the gate exceed the threshold of the control circuit, l. said threshold control circuit including means for producing from said signal gate a display signal gate having an amplitude substantially equal to the minimum amplitude of received signals supplied to said cathode-ray tube means which will actuate the threshold circuit to produce output signals therefrom, m. and means for displaying said display signal gate on sweeps alternating with the sweeps displaying said received signals and having coinciding baselines.

3. Ultrasonic non-destructive pulse testing apparatus which comprises a. pulse generator and transducer means for applying ultrasonic pulses to an object to be tested, b. means for receiving signals corresponding to variations or defects in an object under test, c. cathode-ray tube means for displaying received signals, d. and sweep generator means for producing sweeps of adjustable expansion for said cathode-ray tube means, e. said sweep generator means including means for generating initial ramps of predetermined amplitude and including limiter means having a limit level less than said predetermined amplitude, f. variable attenuator means supplied with said initial ramps and having an output connected to said limiter means for limiting portions of the ramps to a constant level and produce sweeps of adjustable time duration, g. and means for amplifying and supplying the sweeps to said cathode-ray tube means.

4. Apparatus according to claim 3 including means for synchronizing said initial ramps with said ultrasonic pulses.

5. Apparatus according to claim 3 in which the slope of said initial ramps and said limit level are predetermined to limit the initial portions of the ramps to a constant level as said variable attenuator means is adjusted to produce expanded sweeps.

6. Apparatus according to claim 3 including signal gate generating means supplied with said sweeps and comprising clamping means for clamping the peaks of said sweeps at an adjustable first level with respect to a reference level which is less than the sweep amplitude, means for establishing an adjustable second level intermediate said reference and first levels, and switch circuit means responsive to sweeps from said clamping means and said second level for producing one output level during a sweep portion lying in the zone between substantially said reference and second levels and a different output level during sweep portions lying outside said zone, to thereby produce a signal gate.

7. Ultrasonic non-destructive pulse testing apparatus which comprises a. pulse generator and transducer means for applying ultrasonic pulses to an object to be tested,
b. means for receiving signals corresponding to variations or defects in an object under test,
c. cathode-ray tube means for displaying received signals,
d. sweep generator means for producing sweeps of substantially constant peak amplitude and adjustable time duration for said cathode-ray tube means,
e. and signal gate generating means supplied with said sweeps and including clamping means for clamping the peaks of the sweeps at an adjustable first level with respect to a reference level which is less than the sweep amplitude,
f. means for establishing an adjustable second level intermediate said reference and first levels,
g. and switch circuit means responsive to sweeps from said clamping means and said second level for producing one output level during a sweep portion lying in the zone between substantially said reference and second levels and a different output level during sweep portions lying outside said zone, to thereby produce a signal gate.

8. Apparatus according to claim 7 in which said switch circuit means comprises output circuit means biased at said second level, first and second control circuit means responsive to said sweeps from the clamping means for actuating said output circuit means to said different output level during sweep portions before reaching said zone and after leaving the zone, respectively, and for actuating the output circuit means to said one output level during sweep portions lying within said zone.

9. Ultrasonic non-destructive pulse testing apparatus which comprises
a. pulse generator and transducer means for applying ultrasonic pulses to an object to be tested,
b. means for receiving signals corresponding to variations or defects in an object under test,
c. cathode-ray tube means supplied from the receiving means and including sweep means for displaying received signals,
d. a signal gate generator synchronized with said sweep means,
e. an adjustable threshold control circuit supplied with received signals and with the signal gate from said signal gate generator for producing output signals when received signals within the gate exceed the threshold of the control circuit,
f. said threshold control circuit including means for producing from said signal gate a display signal gate having an amplitude substantially equal to the minimum amplitude of received signals supplied to said cathode-ray tube means which will actuate the threshold circuit to produce output signals therefrom,
g. and means for displaying said display signal gate on sweeps alternating with the sweeps displaying said received signals and having coinciding baselines.

10. Apparatus according to claim 9 in which said threshold control circuit includes at least one transistor having an adjustable threshold control voltage applied to one side of the emitter-base path thereof and the received signals applied to the other side of the path, said means for producing the display signal gate including diode means connected between the signal gate supply and the threshold control voltage, the threshold voltage of said diode means being substantially equal to the transistor threshold voltage drop between the point of supply from said receiving means of received signals for display on said cathode-ray tube means and said threshold control voltage.

11. Ultrasonic non-destructive pulse testing apparatus which comprises
a. pulse generator and transducer means for applying ultrasonic pulses to an object to be tested,
b. means for receiving signals corresponding to variations or defects in an object under test,
c. cathode-ray tube means including sweep means for displaying the received signals,
d. a signal gate generator synchronized with said sweep means,
e. means for displaying gates from said signal gate generator on a set of sweeps alternating with a set of sweeps displaying received signals and having coinciding baselines,
f. a marker generator,
g. and means for displaying markers from said marker generator on both sets of alternating sweeps and on said coinciding baselines.

12. Apparatus according to claim 11 in which said pulse generator means includes a square wave generator and a pulse divider for producing driving pulses for said transducer means, and in which said marker generator is supplied from said square wave generator for producing marker pulses at predetermined edges of the square wave.

13. Ultrasonic non-destructive pulse testing apparatus which comprises
a. pulse generator and transducer means for applying ultrasonic pulses to an object to be tested,
b. means for receiving signals corresponding to variations or defects in an object under test,
c. and cathode-ray tube means including sweep means for displaying the received signals,
d. said pulse generator including a sine wave oscillator, a square wave generator and a pulse divider,
e. means for supplying the output of said sine wave oscillator to said square wave generator to produce a square wave of the same frequency,
f. said pulse divider being supplied with said square wave and including transistor means for periodically supplying an excursion of one polarity of the square wave to an output circuit at a PRF which is a sub-multiple of the square wave frequency to thereby produce an output pulse train,
g. a time-constant circuit including a capacitor and resistance means,
h. means for substantially discharging said capacitor during the occurrence of each output pulse and for applying a charging voltage to the time-constant circuit at the end of the pulse,
i. flip-flop means having two output states,
j. control means responsive to one of said states for preventing the production of output pulses by said transistor means and to the other state for allowing such production,
k. and means for initially actuating said flip-flop means to said one state upon application of said charging voltage to the time-constant circuit and thereafter to said other state as the capacitor approaches full charge.

14. Apparatus according to claim 13 in which said control means comprises means for substantially short-circuiting the input to said transistor means in response to said one state of the flip-flop means and removing the short-circuit in said other state.

15. Apparatus according to claim 13 including a marker capacitor supplied from said square wave generator for producing marker pulses at predetermined edges of the square wave, and means for displaying said marker pulses on sweeps of said cathode-ray tube means.

16. Ultrasonic non-destructive pulse testing apparatus which comprises
   a. a pulse generator and transducer means for applying ultrasonic pulses to an object to be tested,
   b. receiving means for receiving signals corresponding to variations or defects in an object under test,
   c. said receiving means including a multi-stage transistor amplifier having an input supplied with received signals and an output for supplying amplified signals to display or indicating means,
   d. each stage of said multi-stage amplifier including a transistor connected as an emitter-follower with approximately unity gain or less and a voltage step-up transformer connecting the output of the emitter-follower to the input of the emitter-follower in the next stage.

17. Apparatus according to claim 16 in which said voltage step-up transformer is an auto-transformer providing a D-C connection between the emitter of the transistor in one stage and the base of the transistor in the next stage, and means for biasing the base of the transistor in the first stage, whereby the bases of successive stages are biased through the base-emitter paths of the preceding stages respectively.

* * * * *

UNITED STATES PATENT AND TRADEMARK OFFICE
CERTIFICATE OF CORRECTION

PATENT NO. : 3,972,228
DATED : August 3, 1976
INVENTOR(S) : Sven E. Mansson

It is certified that error appears in the above-identified patent and that said Letters Patent are hereby corrected as shown below:

Column 1 line 54, for "It has been" read --It has also been--

Column 4 line 27, for "amplifier" read --amplified--

Column 5 line 15, for "C2" read --Q2--

Column 6 line 11, "Q6 is" read --Q6 in--

" " " 57, for "theh" read --the--

Column 7 line 39, for "lines 85" read --line 85--

Column 7 line 53, for "98" read --97--

Column 8 line 54, for "opposite-poled" read --oppositely-poled--

Column 9 line 34, for "shown in" read --shown at--

Column 10 line 18, for "sweeptime" read --sweep time--

Column 10, line 30, for "occurs" read --occur--

" " " 38, for "time" read --times--

Column 11 line 7, for "generatoing" read --generating--

" " " 16, for "portion in" read --portion lying in--

" " " 51, for "of said" read --for said--

Column 15 line 4, for "marker capacitor" read --marker generator--

Signed and Sealed this

Eighth Day of March 1977

[SEAL]

Attest:

RUTH C. MASON
Attesting Officer

C. MARSHALL DANN
Commissioner of Patents and Trademarks